United States Patent [19]
Alas et al.

[11] Patent Number: 6,054,563
[45] Date of Patent: Apr. 25, 2000

[54] PREPARATION OF SOLID, POWDERY RARE EARTH CARBOXYLATES BY EVAPORATION METHOD

[75] Inventors: Michel Alas, Melle, France; Kenan Yunlu, Princeton, N.J.

[73] Assignees: Rhodia Chimie, Courbevoie, Cedex, France; Rhodia Inc., Cranbury, N.J.

[21] Appl. No.: 09/012,468

[22] Filed: Jan. 22, 1998

Related U.S. Application Data

[60] Provisional application No. 60/040,327, Mar. 5, 1997.

[51] Int. Cl.$^7$ ....................................................... C07F 5/00
[52] U.S. Cl. ............................................... 534/16; 534/15
[58] Field of Search ................................................. 534/16

[56] References Cited

U.S. PATENT DOCUMENTS

| | | | |
|---|---|---|---|
| 5,017,539 | 5/1991 | Jenkins et al. | 502/102 |
| 5,220,045 | 6/1993 | Knauf et al. | 556/55 |
| 5,360,898 | 11/1994 | Jordaan et al. | 534/16 |
| 5,449,387 | 9/1995 | Hawkins et al. | 44/364 |
| 5,610,114 | 3/1997 | Robert et al. | 502/115 |
| 5,731,381 | 3/1998 | Apecetche et al. | 526/83 |
| 5,783,676 | 7/1998 | Yunlu | 534/15 |

FOREIGN PATENT DOCUMENTS

| | | | |
|---|---|---|---|
| 0 577 456 A1 | 6/1996 | European Pat. Off. | B01F 15/00 |

OTHER PUBLICATIONS

Patent Abstracts of Japan, Publication No. 61176554, Published Aug. 8, 1986, Applicant: Daiichi Eng KK, "Production of Neodymium Octanoate".

Search Report for equivalent PCT Application No. PCT/US98/04045.

*Primary Examiner*—Deborah D. Carr
*Attorney, Agent, or Firm*—Katherine L. Carleton

[57] ABSTRACT

A process for producing solid, powdery carboxylates of Rare Earths (RE) elements, among them mainly Nd, La, Pr and Ce, where the ligands coordinated to the metal are long-chain, branched carboxylic acids is provided. Preferably, the carboxylic acids are selected from the group consisting of: 2-ethylhexanoic, neodecanoic, versatic and naphthenic acids.

30 Claims, No Drawings

PREPARATION OF SOLID, POWDERY RARE EARTH CARBOXYLATES BY EVAPORATION METHOD

This application claims benefit of Provisional application Ser. No. 60/040,327, filed Mar. 5, 1997.

TECHNICAL FIELD

The present invention relates to methods for producing solid, powdery Rare Earth Carboxylates utilizing solvent evaporation.

BACKGROUND OF THE INVENTION

The production of solid, powdery Rare Earth carboxylates with branched long- chain ligands, (e.g. Rare Earth 2-ethylhexanoate, versatate, neodecanoate or naphthenate) by conventional methods, produces oily, sticky wax-like materials which upon drying (at from about 60 to about 90° C.) are difficult to convert into powdery materials. One reason for this may be the branched structure of these ligands. The two carboxylic acids which are less prone to give powdery solids, versatic and neodecanoic acid, consist of mixtures of neodecanoic acid isomers in addition to their branched nature. Naphthenic acids consist of monocarboxylic acids of different molecular weight and may contain a variety of hydrocarbon impurities. 2-Ethylhexanoic acid (octoic acid) is available in isomer-free form.

Another reason for the sticky consistency may be the fact that during the formation of these materials various impurities remain incorporated into the product and may be difficult to remove by the usual purification steps. Especially, salts such as nitrates, chlorides, sulfates and the like can be trapped in the product if the method does not offer an easy way to extract these salts. In addition, if the solvent medium consists of polar solvents, such as water, or of alcohols, such as methanol or ethanol, or of ethers, such as THF or DME, the final product can also be contaminated with these. One additional source of impurity is the so-called "free acid", which will be present in the product if part of the carboxylic acid starting material remains unreacted. The presence of free acid can prevent formation of powdery materials. For instance, cerium$^{4+}$ octoate is a solid, but in the presence of one molar equivalent of free acid the product is an oil. Because of the complexity of the structure of the final product, even if the theoretical stoichiometry of the reaction does not allow the formation of unreacted acids, the end product may possess a percentage of unreacted acid present.

In other cases, where, instead of powdery materials, stable solutions of Rare Earth carboxylates are of interest, the above mentioned impurities, such as water or free acid, have been discovered to be welcome additives, since they tend to coordinate to the Rare Earth metal and enable the molecule to stay in solution and thus prevent the formation of structurally more sophisticated systems which in turn can precipitate out as waxy materials or viscous oils.

European Patent 0 599 096 A1 (to Michelin; Jun. 1, 1994) describes the preparation of solid neodymium octoate by a precipitation reaction in water from $NdCl_3$ and sodium octoate at 90° C. No information is provided on the consistency of the material.

Most of the literature deals with the preparation of Rare Earth carboxylates with ligands other than 2-ethylhexanoic, neodecanoic, versatic and naphthenic acid. The synthesis of scandium laureate, palmitate, stearate (from $ScCl_3$ and NaOOCR in ethanol) and the synthesis of cerium (III) octanoate (from $Ce(NO_3)_3$ and octanoic acid in water) is reported along with spectroscopic and physical data (from: GMELIN Handbook, Rare Earths Main Vol. D 5).

It is an object of the present invention to provide means for the preparation of solid powdery carboxylates of neodymium 2-ethylhexanoate, neodecanoate, versatate and naphthenate with emphasis on techniques promoting the powdery consistency of these products.

SUMMARY OF THE INVENTION

The present invention relates to the production of solid, powdery carboxylates of Rare Earths (RE) elements, such as Nd, La, Pr and Ce, where the ligands coordinated to the metal are long-chain, branched carboxylic acids. Preferably, the carboxylic acids are selected from the group consisting of: 2-ethylhexanoic, neodecanoic, versatic and naphthenic acids. The process comprises the following steps:

1) Preparation of a concentrated solution of the Rare Earth carboxylate (up to about 12% RE content, preferably neodymium) in a hydrocarbon solvent comprising up to about 3% water as stabilizer and up to 12% free acid or preferably being substantially free of free acid (less than about 1%) or having no free acid; and
2) Azeotropic distillation of the solvent.

Unless otherwise stated, all parts, ratios or percentages are by weight.

Unless otherwise stated, all molecular weights are mass averages.

"Comprising" as used herein, means various components can be conjointly employed. Accordingly, the terms, "consisting essentially of" and "consisting of" are embodied in the term "comprising."

The entire disclosure of the prior provisional application, Ser. No. 60/040,327, is considered as being part of this disclosure and is hereby incorporated by reference.

DETAILED DESCRIPTION OF THE INVENTION

The scope of the invention comprises the preparation of powdery solids of branched, long-chain Rare Earth carboxylates by evaporating a highly concentrated solution to dryness.

Preparation of Rare Earth carboxylate solutions

A method for preparing highly concentrated and stable solutions of the above-mentioned Rare Earth carboxylates is by the reaction of a carboxylate salt with a Rare Earth salt in a two solvent medium, for instance:

Reaction of the carboxylate salt with RE nitrate in water cyclohexane:

| $RE(NO_3)$ + RE nitrate | 3R-COONa → | $RE(OOC-R)_3$ + RE carboxylate dissolved in organic solvent | $3NaNO_3$ Salt by-product dissolved in water |
|---|---|---|---|

(RE = Nd; R = versatate)

Immediately after the addition of the Rare Earth salt, the Rare Earth carboxylate is formed; but, because of its solubility in cyclohexane, it dissolves quickly in the organic layer (the carboxylate solution). However in the absence of any stabilizers, precipitation would occur. The stabilizer to be utilized is water. The water needed for stabilization dissolves in the organic layer. It has been found that the quantity of stabilizing water is dependent on the concentration of the solution. Highly diluted solutions (e.g. from about 2 to about 5% Nd content) require less stabilizer (e.g. about 1% water) while concentrated solutions (e.g., from about 10 to about 12% Nd content) require more of the stabilizing agent (e.g. from about 2 to about 3% water). Generally, the carboxylate solutions can comprise from about 0.005% to about 3%, preferably from about 0.5% to about 3%, and more preferably from about 1% to about 2%, of water. Generally, the carboxylate solutions can comprise from about 0.005% to about 12%, preferably from about 0.005% to about 9%, more preferably from about 0.005% to about 6% and most preferably from about 0.005% to about 3% of free acid. Generally, the carboxylate solutions can comprise from about 2% to about 12%, preferably from about 6% to about 12% and most preferably from about 10% to about 12% RE. The preferred invention relates to highly concentrated, but stable, solutions of Rare Earth carboxylates substantially free of free acid (less than about 1%, preferably less than about 0.5% and most preferably less than about 0.1%) and their ability to produce solid, powdery Rare Earth carboxylates.

The next step of the synthesis is the removal of the aqueous layer by conventional methods and washing of the organic layer preferably with water. The washing step is essential since it removes impurities such as salt by-products and unreacted starting materials, which can prevent, in subsequent steps, the formation of powdery materials.

Removal of the solvent(s) and drying conditions

The final step of the synthesis is the removal of the solvent(s) by evaporation methodology. This is carried out under usual distillation conditions with or without applying any vacuum. Any conventional drying technique or dryer can be utilized. The preferred dryer has features to ensure the formation of a powdery product. These features are high mixing power and an agitator capable of providing homogeneous mixing and promoting even heat transfers. Suitable agitators are described in EP 0577456A1 published Jan. 5, 1994, Bertrand et al. (PIERRE GUERIN S. A.), which is incorporated herein by reference. This results in a low temperature difference between different areas of the material (high heat transfer coefficient), and good renewal of the product because of mechanical stirring which avoids the formation of dead zones.

The solid, powdery Rare Earth carboxylates are useful as catalyst components for the polymerization of conjugated dienes, such as butadiene, isoprene, 1,3 pentadiene or a mixture thereof. Prefereably, the RE carboxylates of the present invention are utilized for the polymerization of butadiene.

Components

The carboxylic acids suitable for use include aliphatic, cycloaliphatic and aromatic mono and polybasic carboxylic acids. The acids may be saturated or unsaturated, straight chained or branched. The organic carboxylic acids can be either natural or synthetic or mixtures thereof. Examples of natural acids, although usually refined, include straight and branched chain carboxylic acids and cyclic carboxylic acids such as naphthenic acid. A variety of synthetic carboxylic acids and particularly aliphatic or alicyclic mono-carboxylic acids or mixtures thereof, are useful. Long chain, branched carboxylic acids are preferred.

The organic carboxylic acids preferably will contain from about 6 to about 32 carbon atoms, preferably from about 5 to about 18 and more preferably from about 8 to about 10, but when more than one of the acids is employed, carboxylic acids containing as little as about 5 carbon atoms or as little as 2 carbon atoms can be employed as one of the acids of the mixtures. Examples of useful organic carboxylic acids include 2-ethyl hexanoic acid, neodecanoic acid, and commercially available mixtures of two or more carboxylic acids such as naphthenic acids. The acid number for the preferred naphthenic acid is from about 160 to about 300 mg KOH/g.

The carboxylic acids for use herein are naphthenic acid (preferably having an acid number of from about 160 to about 300 mg KOH/g), neodecanoic acid (also referred to as versatic acid), and 2-ethyl hexanoic acid.

The term "neodecanoic acid" as utilized herein refers to mixtures of branched carboxylic acids, generally predominately about 10 carbon atoms. These acid mixtures generally have an acid number of from about 310 to about 325 mg KOH/g. Commercially available neodecanoic acids are supplied by Shell under the tradename, "Versatic 10" and by Exxon under the name "Neodecanoic Acid".

These acids are well known and described in, for example Kirk-Othmer, Encyclopedia of Chemical Technology, fourth edition, John Wiley & Son, New York, 1993, Vol.5, pp. 147–192, which is incorporated herein by reference.

The amount of carboxylic acid utilized may vary, although it is generally preferred that the molar equivalent ratio of Rare Earth element to carboxylic acid be at least about 1: about 3 to about 4.

A carboxylic acid salt solution can be prepared by reaction of the carboxylic acid with a base which is an alkali metal, alkaline earth metal or ammonium (preferably tetra (lower alkyl) ammonium) oxide, hydroxide, carbonate or hydrogen carbonate.

The base suitable for reaction is preferably a hydroxide of an alkali metal of Group I, preferably lithium, sodium or potassium. Most preferably the base is a hydroxide of sodium.

Bases suitable for use include: sodium hydroxide, lithium hydroxide, potassium hydroxide, tetrabutyl ammonium hydroxide, tetra methyl ammonium hydroxide, and tetra ethyl ammonium hydroxide.

The reaction of carboxylic acid and base preferably occurs in the presence of water to form the carboxylic salt solution.

The carboxylic salt, preferably in the form of a salt solution, is then preferably reacted with a Rare Earth nitrate (RE $(NO_3)_3$) to produce the Rare Earth carboxylate. This is preferably performed in a reaction media of water and hydrocarbon solvent. The Rare Earth nitrates suitable for use are the nitrates of Group III B of the periodic table (lanthanide series). Suitable Rare Earth nitrates are, for example, the nitrates of lanthanum, cerium, praseodymium, neodymium, promethium, samarium, europium, gadolinium, terbium, dysprosium, holmium, erbium, thulium, ytterbium and lutetium. Due to their similar properties, yttrium and scandium can also be utilized. Preferred for use are the nitrates of neodymium, lanthanum, praseodymium and cerium (preferably Ce III). Most preferred are the nitrates of neodymium. Other Rare Earth water soluble salts can be utilized such as Rare Earth chlorides.

It is most desirable to perform the reaction of the carboxylic salt with a Rare Earth nitrate in a two solvent medium comprising water and a hydrocarbon solvent such as n-hexane, cyclohexane or toluene. The hydrocarbon solvents for use can be aliphatic, cyclic (alicyclic), or branched hydrocarbons, such as butane, pentane, hexane, cyclohexane, heptane or toluene or a mixture thereof. It is preferable that the hydrocarbon solvent be inert (nonreactive) low boiling or relatively low boiling in nature.

While specific embodiments of the invention are described in the Examples, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and equivalents thereof.

Example 1: Preparation of solid neodymium versatate

In a 50 liter Turbosphere® dryer reactor (available from PIERRE GUERIN S.A.) the following charges are made: Water 4 kg, and caustic soda solution 2.48 liters (concentration 298 g/l): The agitation is started and versatic acid (MW=173) 3.2 kg is fed over about 10 minutes. At the clear solution, it is added 20.56 liters of hexane and the mixture is brought to 35° C. 2.1 liters of an aqueous solution of neodymium nitrate ($Nd_2O_3$ content 497 g/l) is added over about 30 minutes. The mixture is agitated during the 30 minutes. The aqueous layer is removed. The upper organic layer is washed once with 4.8 liter of water and distilled under atmospheric pressure up to 85° C. Then the pressure is gradually reduced down to about 30 Torrs. A bluish powder of neodymium versatate is obtained (3.9 kg).

Example 2: Solid Neodymium Ethyl Hexanoate in a Turbosphere Dryer

In a 10 liter Turbosphere® dryer reactor (available from PIERRE GUERIN S. A.) the following charges are made: water 1500 gr, caustic soda anhydrous 278 gr. The agitation is started and 1000 gr of ethyl hexanoic acid (MW=144) are fed over 10 minutes. At the clear solution, it is added 3600 gr of toluene and the mixture is brought to from about 30 to about 50° C. 1364 gr of an aqueous solution of neodymium nitrate (concentration 497 gr or Nd2O3 /l) is added over 30 minutes. The mixture is agitated during the 30 minutes then decanted. The aqueous layer is removed. The upper organic layer is washed once with 1200 gr of water and distilled under vacuum up to about 90° C. A bluish powder of neodymium ethylhexanoate is obtained (1400 gr).

Example 3: Polymerization of butadiene with solid neodymium versatate

A 2 liter stainless steel reactor is charged with 350 ml cyclohexane (water content 35 ppm) and with 40 g of butadiene. To this solution is then added a catalyst mixture consisting of 0.19 g solid Nd versatate as prepared according to Example 1, 1.5 ml of di-ethlyaluminumchloride (1 m solution in hexane) and 5 ml of di-isobutylaluminumhydride (1 m solution in cyclohexane). The temperature is raised to 85° C. in the next 30 min. and cooled down to room temperature in the next 45 minutes. The produced polymer is precipitated out by using 500 ml methanol which contains 0.5g of BHT.

Yield of polybutadiene: 38.4g (96 %)
Isomer composition: cis 98.5 %; trans 1.3 %; vinyl 0.2 %
Mol. weight: 113,000

What is claimed is:

1. A process for preparing solid, powdery Rare Earth carboxylates comprising the steps of:
    a) reaction of a carboxylate salt and a Rare Earth (RE) nitrate or other water soluble RE salt in a solvent comprising: water and a hydrocarbon solvent;
    b) removal and washing of the organic layer to produce a solution of a Rare Earth (RE) carboxylate comprising up to about 12% by weight Rare Earths, up to about 3% by weight water and up to about 12% by weight free acid; and
    c) removal of the remaining solvent by evaporation.

2. The process of claim 1 wherein the carboxylate salt is a salt of carboxylic acids selected from the group consisting of: naphthenic acid, neodecanoic acid, versatic acid, 2-ethyl hexanoic acid and mixtures thereof.

3. The process of claim 2 wherein RE is selected from Group IIIB of the periodic table.

4. The process of claim 3 wherein RE is selected from the group consisting of lanthanum, cerium, praseodymium, neodymium, promethium, samarium, europium, gadolinium, terbium, dysprosium, holmium, erbium, thulium, ytterbium, lutetium, yttrium and scandium.

5. The process of claim 4 wherein RE is selected from neodymium, lanthanum, praseodymium and cerium.

6. The process of claim 5 wherein RE is neodymium.

7. The process of claim 6 wherein the solution of RE carboxylate comprises from about 0.005% to about 3% by weight water, from about 0.005% to about 12% by weight free acid and from about 2% to about 12% by weight RE.

8. The solution of claim 1 wherein the free acid is less than about 1%.

9. A Rare Earth Carboxylate prepared by the process of claim 1.

10. A Rare Earth carboxylate solution comprising:
    a) a Rare Earth (RE) carboxylate,
    b) a hydrocarbon solvent, and
    c) from about 0.005% to about 3% by weight water, and
    d) from about 0.005% to about 12% by weight free acid; and wherein the Rare Earth (RE) content is up to about 12%, by weight.

11. The solution of claim 10 wherein the RE carboxylate is selected from the group consisting of: RE 2-ethylhexanoate, RE versatate, RE neodecanoate, RE naphtehenate and mixtures thereof.

12. The solution of claim 11 wherein RE is selected from Group IIIB of the periodic table and yttrium and scandium.

13. The solution of claim 11 wherein RE is selected from lanthanum, cerium, praseodymium, neodymium, promethium, samarium, europium, gadolinium, terbium, dysprosium, holmium, erbium, thulium, ytterbium and lutetium.

14. The solution of claim 13 wherein RE is selected from neodymium, lanthanum, praseodymium and cerium.

15. The solution of claim 14 wherein RE is neodymium.

16. The solution of claim 15 wherein the free acid is less than about 1% by weight.

17. The solution of claim 11 wherein the free acid is selected from the group consisting of naphthenic acid, neodecanoic acid, versatic acid, and 2-ethylhexanoic acid.

18. A process for preparing powdery Rare Earth Carboxylates comprising the steps of:
    a) reaction of a Rare Earth Nitrate and a carboxylate salt of naphthenic acid, neodecanoic acid, versatic acid, 2-ethylhexanoic acid or mixtures thereof, in a two solvent media comprising water and a hydrocarbon solvent;
    b) removal and washing of the organic layer; and
    c) removal of the solvents by evaporation.

19. The process of claim 18 wherein RE is selected from Group IIIB of the periodic table, scandium and yttrium.

20. The process of claim 19 wherein RE is selected from lanthanum, cerium, praseodymium, neodymium, promethium, samarium, europium, gadolinium, terbium, dysprosium, holmium, erbium, thulium, ytterbium and lutetium.

21. The process of claim 20 wherein RE is selected from neodymium, lanthanum, praseodymium and cerium.

22. The process of claim 21 wherein RE is neodymium.

23. The process of claim 18 wherein the free acid in the organic layer after step b is less than about 1% free acid.

24. The process of claim 18 wherein the free acid is selected from the group consisting of naphthenic acid, neodecanoic acid, versatic acid, and 2-ethylhexanoic acid.

25. A Rare Earth carboxylate prepared by the process of claim 18.

26. A process for the polymerization of one or more conjugated diene monomers by means of a catalyst comprising a RE carboxylate prepared by the process of claim 1.

27. A process according to claim 26 wherein the conjugated diene is butadiene, isoprene, 1,3 pentadiene or a mixture thereof.

28. A process for polymerization of butadiene by means of a catalyst comprising a RE carboxylate prepared by the process of claim 1.

29. A process for the polymerization of one or more conjugated diene monomers by use of a catalyst comprising a RE carboxylate prepared by the process of claim 18.

30. A process for the polymerization of butadiene by use of a catalyst comprising a RE carboxylate prepared by the process of claim 18.

* * * * *